(12) United States Patent
Karidis et al.

(10) Patent No.: US 7,545,647 B2
(45) Date of Patent: *Jun. 9, 2009

(54) COMPLIANT THERMAL INTERFACE STRUCTURE UTILIZING SPRING ELEMENTS

(75) Inventors: John P. Karidis, Ossining, NY (US); Mark D. Schultz, Ossining, NY (US); Bucknell C. Webb, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/037,067

(22) Filed: Feb. 25, 2008

(65) Prior Publication Data

US 2008/0144288 A1    Jun. 19, 2008

Related U.S. Application Data

(63) Continuation of application No. 11/151,830, filed on Jun. 14, 2005, now Pat. No. 7,355,855.

(51) Int. Cl.
*H05K 7/20* (2006.01)
*H01L 23/36* (2006.01)

(52) U.S. Cl. .......... 361/710; 361/704; 361/715; 165/80.3; 165/104.33; 165/185; 257/707; 257/713; 257/722

(58) Field of Classification Search .......... 361/676, 361/677, 679, 690–704, 707, 709–712, 713–728, 361/739, 743, 760–764; 165/80.3, 104.33, 165/80.2, 80.4, 185; 174/15.1, 16.3, 252; 257/718–727

See application file for complete search history.

(56) References Cited

U.S. PATENT DOCUMENTS

| | | | | |
|---|---|---|---|---|
| 4,415,025 A | * | 11/1983 | Horvath | 165/185 |
| 4,479,140 A | * | 10/1984 | Horvath | 257/713 |
| 5,052,481 A | * | 10/1991 | Horvath et al. | 165/185 |
| 5,159,531 A | * | 10/1992 | Horvath et al. | 361/704 |
| 5,270,902 A | * | 12/1993 | Bellar et al. | 361/718 |
| 5,291,371 A | * | 3/1994 | Gruber et al. | 361/705 |
| 5,528,456 A | * | 6/1996 | Takahashi | 361/704 |
| 5,548,090 A | * | 8/1996 | Harris | 174/252 |
| 5,557,501 A | * | 9/1996 | DiStefano et al. | 361/704 |
| 6,081,428 A | * | 6/2000 | Fujimoto | 361/719 |
| 6,411,513 B1 | * | 6/2002 | Bedard | 361/704 |
| 6,462,952 B1 | * | 10/2002 | Ubukata et al. | 361/719 |
| 7,064,953 B2 | * | 6/2006 | Miller | 361/690 |

* cited by examiner

*Primary Examiner*—Michael V Datskovskiy
(74) *Attorney, Agent, or Firm*—Michael J. Buchenhorner; Vazken Alexanian

(57) ABSTRACT

A structure for cooling an electronic device is disclosed. The structure includes a solid heat-conducting layer disposed over the electronic device. The solid heat-conducting layer is a planar surface in contact with the electronic device. The structure further includes a plurality of copper spring elements disposed between the solid heat-conducting layer and the electronic device for providing a heat path from the electronic device and wherein the plurality of spring elements extend in an upper direction away from the electronic device and wherein the plurality of spring elements include a spring for offering resistance when loaded and wherein the spring elements have a smaller profile at a first end in contact with the electronic device, wherein the profile increases in size at a second end in contact with the solid heat-conducting layer.

5 Claims, 18 Drawing Sheets

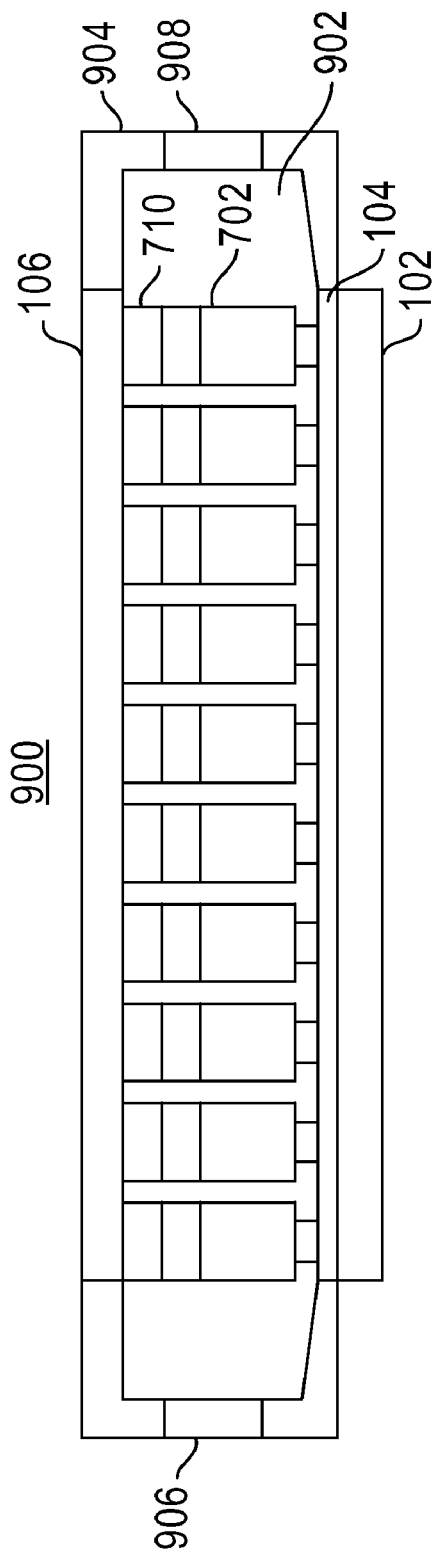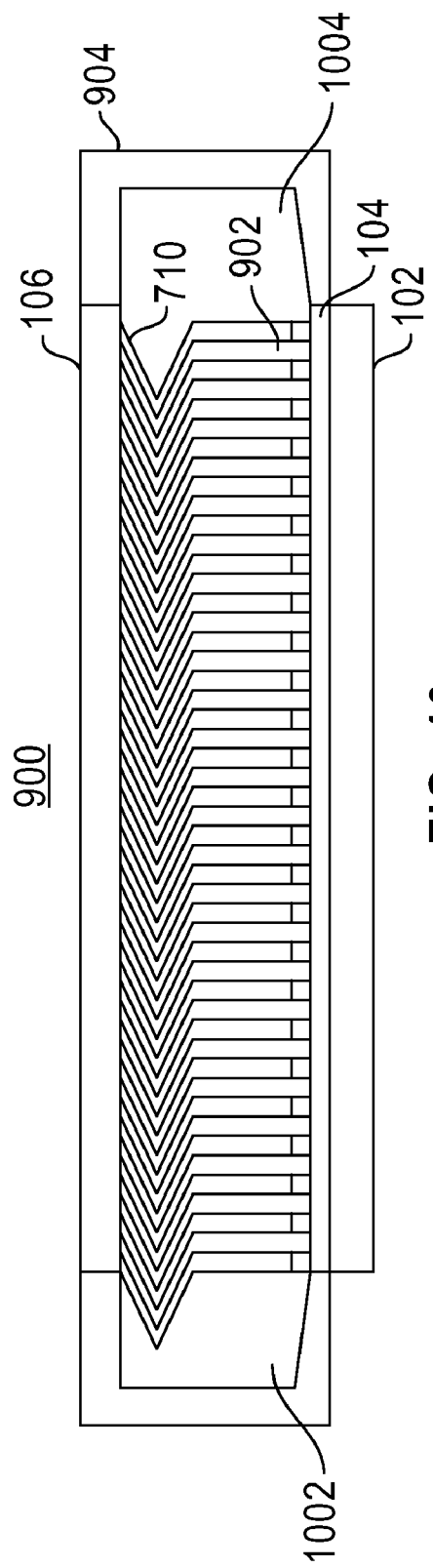

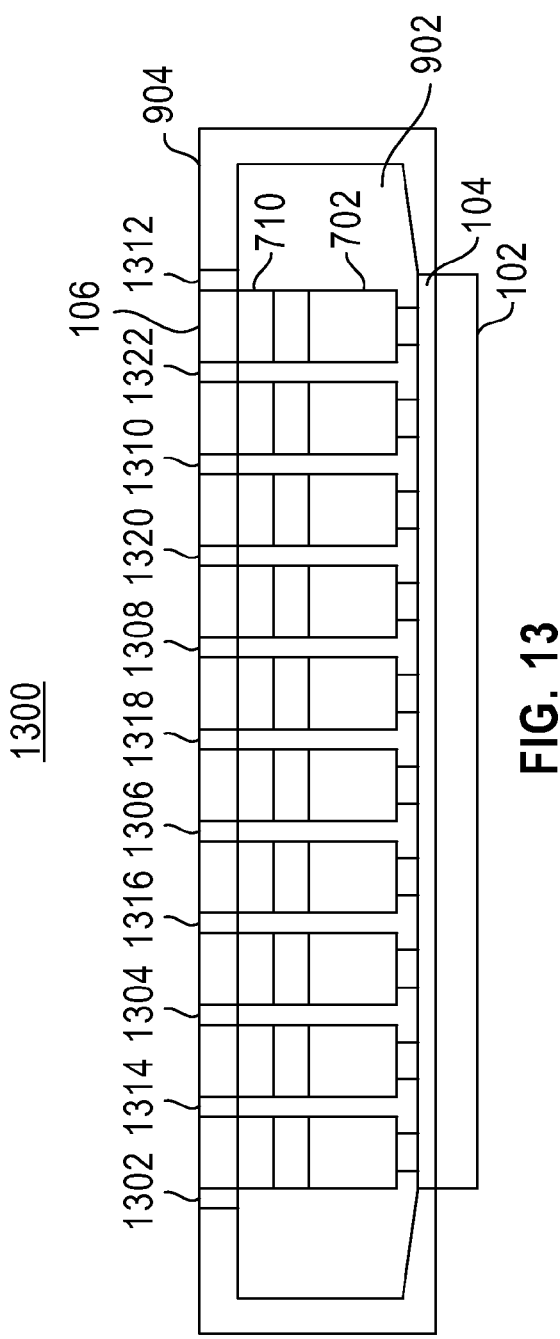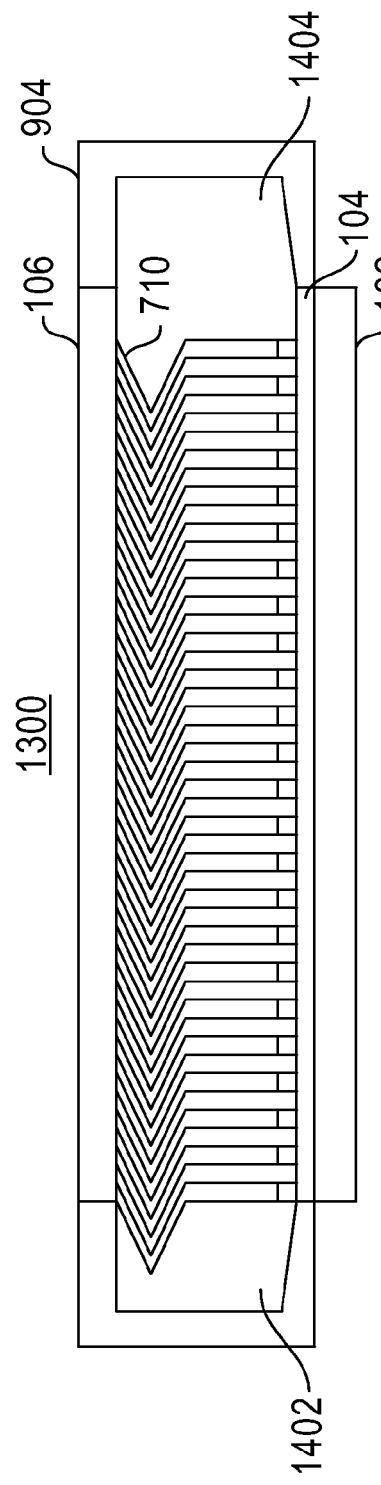

COMPLIANT THERMAL INTERFACE STRUCTURE UTILIZING SPRING ELEMENTS

CROSS-REFERENCE TO RELATED APPLICATIONS

This application is a continuation of commonly-owned, U.S. application Ser. No. 11/151,830, filed Jun. 14, 2005, now U.S. Pat. No. 7,355,855, which is incorporated by reference as if fully set forth herein.

STATEMENT REGARDING FEDERALLY SPONSORED-RESEARCH OR DEVELOPMENT

None.

INCORPORATION BY REFERENCE OF MATERIAL SUBMITTED ON A COMPACT DISC

None.

FIELD OF THE INVENTION

The invention disclosed broadly relates to the field of cooling devices for electronic components, and more particularly relates to the field of heat sinks for microprocessors.

BACKGROUND OF THE INVENTION

During the normal operation of a computer, integrated circuit devices generate significant amounts of heat. This heat must be continuously removed, or the integrated circuit device may overheat, resulting in damage to the device and/or a reduction in operating performance. Cooling devices, such as heat sinks, have been used in conjunction with integrated circuit devices in order to avoid such overheating. Generally, a passive heat sink in combination with a system fan has provided a relatively cost-effective cooling solution. In recent years, however, the power of integrated circuit devices such as microprocessors has increased exponentially, resulting in a significant increase in the amount of heat generated by these devices, thereby necessitating a more efficient cooling solution.

It is becoming extremely difficult to extract the heat generated by semiconductor devices (processors, in particular) that continue to generate more and more heat in the same amount of space. Heat is typically extracted by coupling a heat spreader and thermal cap to the semiconductor and a heat sink. This coupling typically involves a thermal paste which serves to not only transfer heat but provide some degree of mechanical compliance to compensate for dimensional changes driven by the high temperatures. This paste is often a weak link in the thermal path. Attempts to thin this layer have resulted in failure of the layer when it is exposed to dimensional changes due to heat.

One approach to this problem involves a spring loaded assembly of fingers with thermal paste in between them and a thermal paste interface to the chip. This solution is limited in performance by the thermal paste and in design by the requirement for consistent spring loading. Liquid metal has been proposed on its own as a thermal interface material, but could have significant difficulty dealing with large z-axis thermally induced excursions, requiring some compliance elsewhere in the package or (if the largest spacing seen is still thermally acceptable) some sort of edge reservoir design.

Therefore, a need exists to overcome the problems with the prior art as discussed above, and particularly for a way to cool small electronic devices using a thermally compliant material.

SUMMARY OF THE INVENTION

Briefly, according to an embodiment of the invention a structure for cooling an electronic device is disclosed. The structure includes a solid heat-conducting layer disposed over the electronic device. The solid heat-conducting layer is a planar surface in contact with the electronic device. The structure further includes a plurality of spring elements formed from a heat-conducting material and disposed between the solid heat-conducting layer and the electronic device for providing a heat path from the electronic device and wherein the plurality of spring elements extend in an upper direction away from the electronic device and wherein the plurality of spring elements include a spring for offering resistance when loaded and wherein the spring elements have a smaller profile at a first end in contact with the electronic device, wherein the profile increases in size at a second end in contact with the solid heat-conducting layer.

BRIEF DESCRIPTION OF THE DRAWINGS

To describe the foregoing and other exemplary purposes, aspects, and advantages, we use the following detailed description of an exemplary embodiment of the invention with reference to the drawings, in which:

FIG. 9 is a cross-sectional side view of a cooling structure for an electronic device, the cooling structure including spring elements with a fin, a plate and a liquid, according to one embodiment of the present invention;

FIG. 10 is another cross-sectional side view of the cooling structure of FIG. 9;

FIG. 13 is a cross-sectional side view of a cooling structure for an electronic device, the cooling structure including spring elements with a fin, a plate, liquid inlets/outlets and a liquid, according to one embodiment of the present invention;

FIG. 14 is another cross-sectional side view of the cooling structure of FIG. 13;

Figure 1:
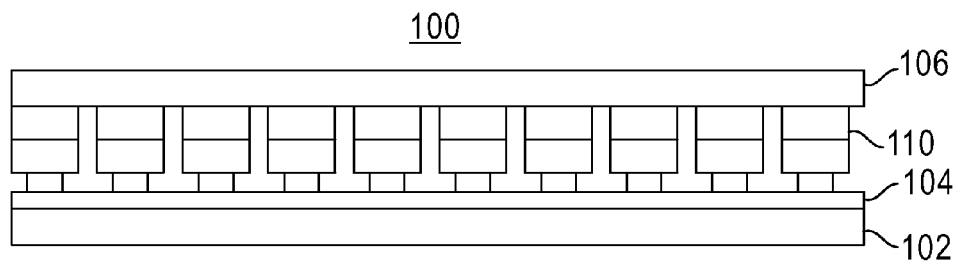
FIG. 1 is a cross-sectional side view of a cooling structure for an electronic device, the cooling structure including spring elements and a plate, according to one embodiment of the present invention.

While the invention as claimed can be modified into alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the scope of the present invention.

DETAILED DESCRIPTION

The present invention includes an array of high thermal conductivity spring elements (made of copper, for example) with a high packing density, wherein the spring elements are attached to or integrated with a thermally conductive plate having either a flexible or somewhat rigid top (such as a heat sink or cold cap side). In another embodiment of the present invention, the array of spring elements can be either coupled or placed in contact with (directly or via an interface material) a subject electronic device, such as a semiconductor device.

In another embodiment of the present invention, the array of spring elements can be coupled to or integrated with a conformable high thermal conductivity bottom membrane. When coupled with a membrane, the array of spring elements can have a relatively small contact area that rapidly increases in cross section to the full cross section of the spring element. This arrangement prevents the end of the spring elements from adding unwanted rigidity to the conformable membrane with minimal thermal resistance. Similarly, the narrowing cross-section feature can also be implemented in the case where the array of spring elements are either coupled or placed in contact with a subject electronic device. However, if a very thin thermal interface material is present between the array of spring elements and the electronic device and there is high spatial frequency content in the lack of flatness of the electronic device surface, it may be desirable to narrow the spring element ends.

In another embodiment of the present invention, if pure perpendicular motion is desirable upon compression in the case where the array of spring elements are coupled to or integrated with a conformable high thermo conductivity bottom membrane, the array of spring elements may have narrow sections at the ends where they contact a heat sink. Packing density can be as high as practical without interference within an expected compliance range. In another embodiment of the present invention, the array of spring elements can be a particular thickness through their entire length.

In another embodiment of the present invention, if the space occupied by the array of spring elements can be sealed without compromising compliance, a thermally conductive liquid (such as liquid metal) can be added to reduce the thermal path length. In this embodiment, the present invention takes advantage of useful thermal and physical characteristics of liquid metal. Liquid metal is used as a thermal interface material between the array of spring elements and a microprocessor or a plate coupled thereto.

The present invention is advantageous as it provides compliance in a location other than (or in addition to) the gap area between the microprocessor and the heat conducting portion of the invention neighboring the microprocessor. The present invention is further advantageous as the forces on the microprocessor exerted by physical changes brought on by heat in the x, y and z directions do not vary greatly. Further, the present invention allows for z-compliance by utilizing the array of spring elements. Thus, the present invention eliminates the necessity for compliance in a film disposed between the microprocessor and a heat spreader or heat sink. Additionally, the present invention does not require the use of high-viscosity thermal paste, which is not effective in very thin layers.

FIG. 1 is a cross-sectional side view of a cooling structure for an electronic device, the cooling structure including spring elements and a plate, according to one embodiment of the present invention. FIG. 1 shows a heat-producing electronic device, a microprocessor 102, located along the bottom of the assembly 100. Disposed on the microprocessor 102 is a first layer 104, which can be a solid layer for providing a heat path from the microprocessor 102 to the upper elements of the assembly 100. Examples of a solid heat-conducting layer used for this purpose are a thermally conductive adhesive and a solder such as indium. The first layer 104 is a planar surface that rests in contact with the microprocessor 102. In another embodiment of the present invention, the first layer 104 can be a conformable high thermal conductivity membrane such as a copper sheet. In an embodiment where the first layer 104 is a membrane, an additional layer of high thermal conductivity material would be disposed between the microprocessor 102 and the membrane.

The cooling structure assembly 100 further includes an array of spring elements 110 that are in contact with or are coupled with the first layer 104. The array of spring elements 110 includes a plurality of springs extending in the upper direction away from the source of the heat, the microprocessor 102. Each of the spring elements 110 draw heat away from the microprocessor 102 and allows the heat to radiate out from the increased surface area of the spring elements 110. Each of the spring elements 110 is formed of a heat conducting material such as copper. Further, each of the array of spring elements 110 exhibits qualities of a spring, which allows for compression and elongation in the z-direction, i.e., the up and down direction, and in the x, y-directions, i.e., the sideways directions. This provides heat compliance in accordance with dimensional changes in the microprocessor 102 during use.

Each of the array of spring elements 110 comprises a spring such as a leaf spring or a helix spring for offering resistance when loaded. Each of the array of spring elements 110 provide compliance between the top layer 106 and the microprocessor 102 and works to keep the top layer 106 in close proximity to the microprocessor 102. The composition and shape of each of the array of spring elements 110 is described in greater detail below.

The cooling structure assembly 100 further includes a top layer 106 comprising a planar surface, wherein the array of spring elements 110 contact the top layer 106. The top layer 106 can be a solid layer for providing a heat path from the microprocessor 102 to the upper elements of the assembly 100. The top layer 106 can be a solid heat-conducting layer such as a thermally conductive adhesive, solder, or solid metal structure.

Figure 2:
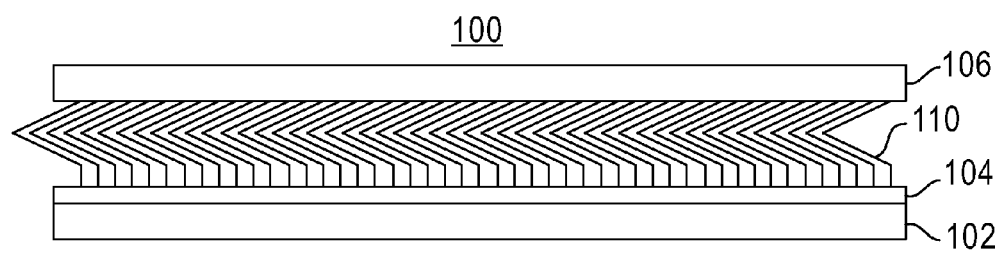
FIG. 2 is another cross-sectional side view of the cooling structure of FIG. 1.

FIG. 2 is another cross-sectional side view of the cooling structure of FIG. 1. FIG. 2 shows the cooling structure assembly 100 comprising the top layer 106, the first layer 104 and the array of spring elements 110 disposed between them. FIG. 2 also shows the microprocessor 102 at the bottom of the cooling structure assembly 100.

Figure 3:
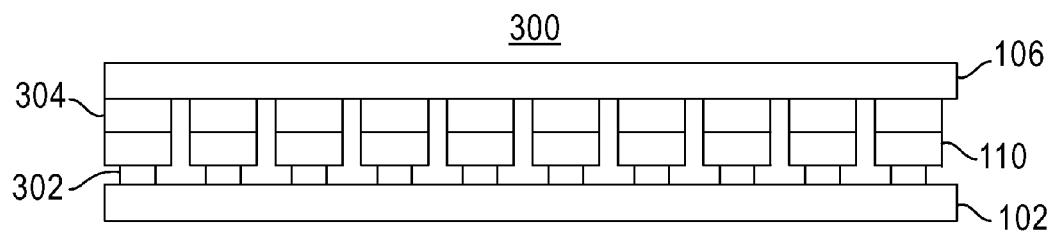
FIG. 3 is a cross-sectional side view of a cooling structure for an electronic device, the cooling structure including spring elements, according to one embodiment of the present invention.

FIG. 3 is a cross-sectional side view of a cooling structure for an electronic device, the cooling structure including spring elements, according to one embodiment of the present invention. FIG. 3 shows the cooling structure assembly 300 comprising the top layer 106, the microprocessor 102 at the bottom of the cooling structure assembly 300 and the array of spring elements 110 disposed between them. The cooling structure assembly 300 of FIG. 3 is similar to the cooling structure assembly 100 of FIG. 1 except for the presence of the first layer 104.

In this embodiment of the present invention, the array of spring elements 110 are either coupled or placed in contact with (directly or within an interface material) the microprocessor 102. In another embodiment, the array of spring elements 110 can have a relatively small profile at the end 302 of the spring elements that contact the microprocessor 102. The profile would rapidly increase in size to the full cross section of the spring element at the end 304 of the spring elements that contact the top layer 106. This arrangement prevents the end 302 of the array of spring elements 110 from adding unwanted rigidity to the microprocessor 102 without any substantial thermal resistance. In another embodiment, if a very thin thermal interface material is present between the array of spring elements 110 and the microprocessor 102 and there is high spatial frequency content in the lack of flatness of the surface of the microprocessor 102, it may be desirable to narrow the spring element ends. In another embodiment of the present invention, the array of spring elements 110 can be a particular thickness through their entire length.

Figure 4:
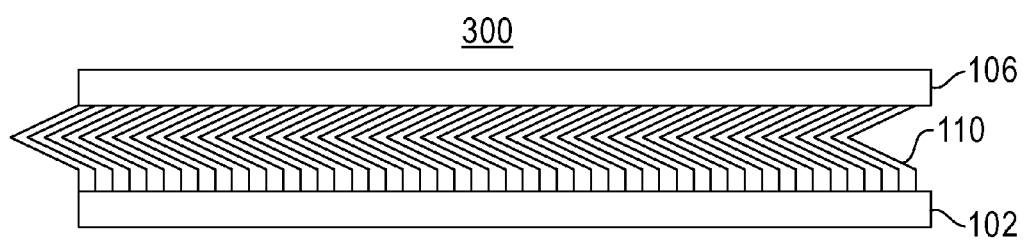
FIG. 4 is another cross-sectional side view of the cooling structure of FIG. 3.

FIG. 4 is another cross-sectional side view of the cooling structure of FIG. 3. FIG. 4 shows the cooling structure assembly 300 comprising the top layer 106, the microprocessor 102 at the bottom of the cooling structure assembly 300 and the array of spring elements 110 disposed between them.

Figure 5:
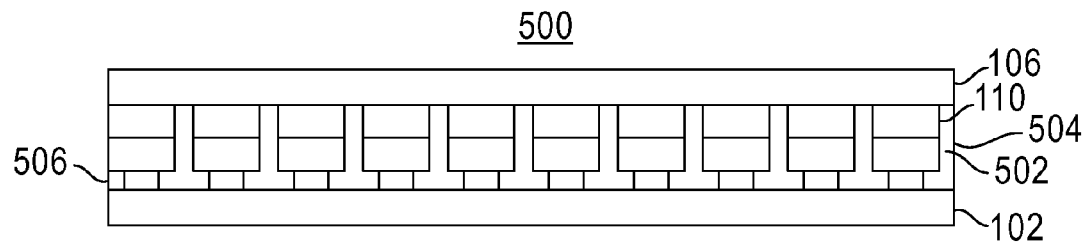
FIG. 5 is a cross-sectional side view of a cooling structure for an electronic device, the cooling structure including spring elements and a liquid, according to one embodiment of the present invention.

FIG. 5 is a cross-sectional side view of a cooling structure for an electronic device, the cooling structure including spring elements and a liquid, according to one embodiment of the present invention. FIG. 5 shows the cooling structure assembly 500 comprising a top layer 106, a microprocessor 102 at the bottom of the cooling structure assembly 500 and an array of spring elements 110 disposed between them. Also included is a thermal interface material 502 and a seal 504 for containing the thermal interface material 502. The cooling structure assembly 500 of FIG. 5 is similar to the cooling structure assembly 300 of FIG. 3 except for the presence of the thermal interface material 502 and the seal 504. In this embodiment of the present invention, the array of spring elements 110 are either coupled or placed in contact with (directly or within an interface material) the microprocessor 102.

The thermal interface material 502 can be a liquid material or a non-rigid solid material. In one embodiment, the thermal interface material 502 is a non-metal liquid, such as oil or water, or a liquid metal such as mercury, gallium or a gallium alloy such as with tin or indium. A liquid 502 can be sealed with a seal 504 or container so as to restrict the escape of the liquid from the desired area over the microprocessor 102. The liquid nature of the liquid 502 allows the substance to fill the areas created by the gap created between each of the spring elements 110. The liquid 502 provides a heat path from the microprocessor 102 to the upper elements of the assembly 500 as the heat travels from the microprocessor 102 to the top layer 106.

Figure 6:
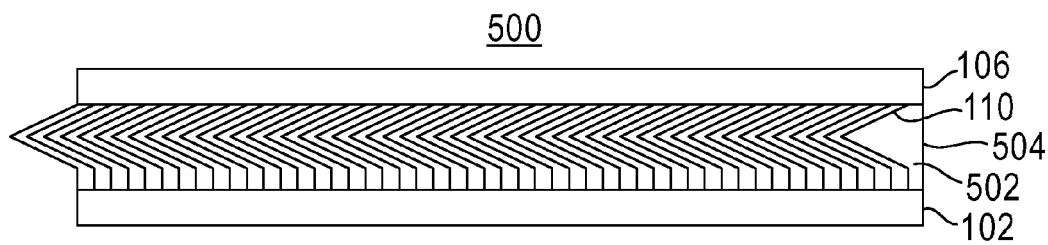
FIG. 6 is another cross-sectional side view of the cooling structure of FIG. 5.

FIG. 6 is another cross-sectional side view of the cooling structure of FIG. 5. FIG. 6 shows the cooling structure assembly 500 comprising a top layer 106, a microprocessor 102 at the bottom of the cooling structure assembly 500 and an array of spring elements 110 disposed between them. Also included is a thermal interface material 502 and a seal 504 for containing the thermal interface material 502.

Figure 7:
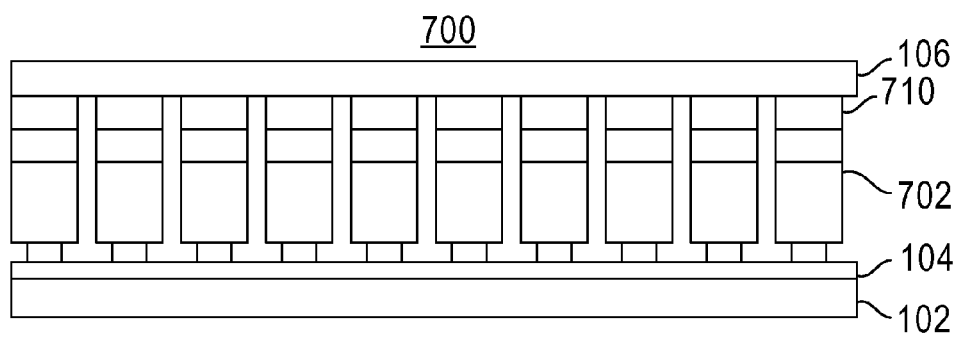
FIG. 7 is a cross-sectional side view of a cooling structure for an electronic device, the cooling structure including spring elements with fins and a plate, according to one embodiment of the present invention.

FIG. 7 is a cross-sectional side view of a cooling structure for an electronic device, the cooling structure including spring elements with fins and a plate, according to one embodiment of the present invention. FIG. 7 shows the cooling structure assembly 700 comprising the top layer 106, the first layer 104 and the array of spring elements 710 disposed between them. FIG. 7 also shows the microprocessor 102 at the bottom of the cooling structure assembly 700. In another embodiment of the present invention, the first layer 104 can be a conformable high thermal conductivity membrane such as a copper sheet. In an embodiment where the first layer 104 is a membrane, an additional layer of high thermal conductivity material would be disposed between the microprocessor 102 and the membrane. The cooling structure assembly 700 of FIG. 7 is similar to the cooling structure assembly 100 of FIG. 1 except for the presence of the elongated fin portion 702 of each of the array of spring elements 710.

In another embodiment of the present invention, a coolant would flow between and among the array of spring elements 710. The coolant can be a liquid material or a gas material. In one embodiment, the coolant is a non-metal liquid, such as oil or water, or a liquid metal such as mercury, gallium or a gallium alloy such as with tin or indium. The liquid nature of the liquid allows the substance to fill the areas created by the gap created between each of the spring elements 710. The liquid provides a heat path from the microprocessor 102 to the upper elements of the assembly 700 as the heat travels from the microprocessor 102 to the top layer 106.

The portion 702 of each of the array of spring elements 710 comprises a plurality of fins extending in the upper direction away from the source of the heat, the microprocessor 102. The inclusion of the fins serves to effectively increase the surface area of the surface of the first layer 104, which serves to dissipate heat into a cooling gas or liquid. Each fin draws heat away from the microprocessor 102 and allows the heat to be conducted out from the increased surface area of the fins. The first layer 104 is a planar surface that rests in contact with the microprocessor 102.

Figure 8:
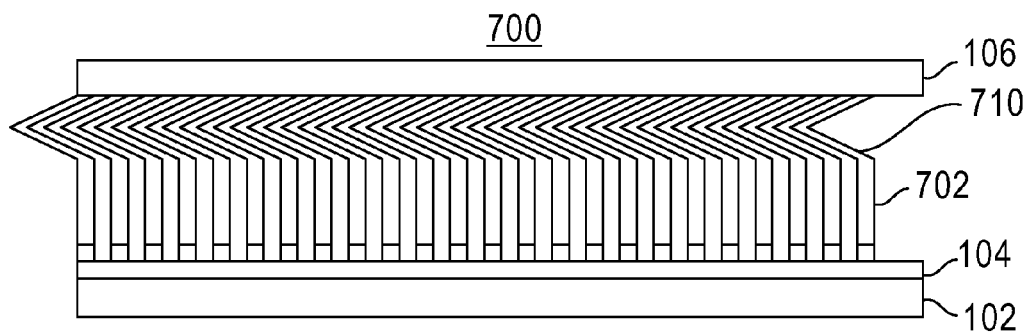
FIG. 8 is another cross-sectional side view of the cooling structure of FIG. 7.

FIG. 8 is another cross-sectional side view of the cooling structure of FIG. 7. FIG. 8 shows the cooling structure assembly 700 comprising the top layer 106, the first layer 104 and the array of spring elements 710 disposed between them. FIG. 8 also shows the microprocessor 102 at the bottom of the cooling structure assembly 700.

FIG. 9 is a cross-sectional side view of a cooling structure for an electronic device, the cooling structure including spring elements with a fin, a plate and a liquid, according to one embodiment of the present invention. FIG. 9 shows the cooling structure assembly 900 comprising the top layer 106, the first layer 104 and the array of spring elements 710 disposed between them. FIG. 9 also shows the microprocessor 102 at the bottom of the cooling structure assembly 900, a cooling gas or liquid 902 (i.e., coolant), a seal 904 and a cooling gas or liquid inlet/outlet pair 906 and 908. The cooling structure assembly 900 of FIG. 9 is similar to the cooling structure assembly 700 of FIG. 7 except for the provisions for handling a coolant 902, such as seal 904 and inlet/outlet pair 906 and 908. The cooling structure 900 can also include a pair of flow-restricting end-plates (not shown in this figure but described in greater detail below).

The coolant 902 can be a gas, a non-metal liquid material, such as oil or water, or a metal liquid material such as mercury, gallium or a gallium alloy such as with tin or indium. The coolant 902 is described in greater detail with reference to FIG. 7 above.

FIG. 9 also shows an inlet/outlet pair 906 and 908 for allowing ingress and egress of the coolant 902. The inlet 906 allows for the intake of the coolant 902 as it is pumped or otherwise pushed or propelled into the assembly 900. As the coolant 902 travels in the space filling the areas created by the gap created between the microprocessor 102 and the top layer 106, the coolant 902 absorbs the heat emanated from the first layer 104 and the array of spring elements 710, including the fin structure 702. The outlet 908 allows for the egress of the coolant 902 as it is pumped or otherwise pulled or propelled out of the assembly 900 for cooling and eventual recycling into the assembly 900.

FIG. 10 is another cross-sectional side view of the cooling structure of FIG. 9. FIG. 10 shows the cooling structure assembly 900 comprising the top layer 106, the first layer 104 and the array of spring elements 710 disposed between them. FIG. 10 also shows the microprocessor 102 at the bottom of the cooling structure assembly 900, a coolant 902 and a seal 904. The cooling structure 900 can also include a pair of flow-restricting end-plates 1002 and 1004 that fill the area on either end of the array of spring elements 710 in FIG. 10. The purpose of the end-plates 1002 and 1004 is to restrict the flow of the coolant 902 into those spaces so as to force the coolant 902 to flow in the area between the multiple spring elements, which is where a higher degree of heat dissipation occurs.

Figure 11:
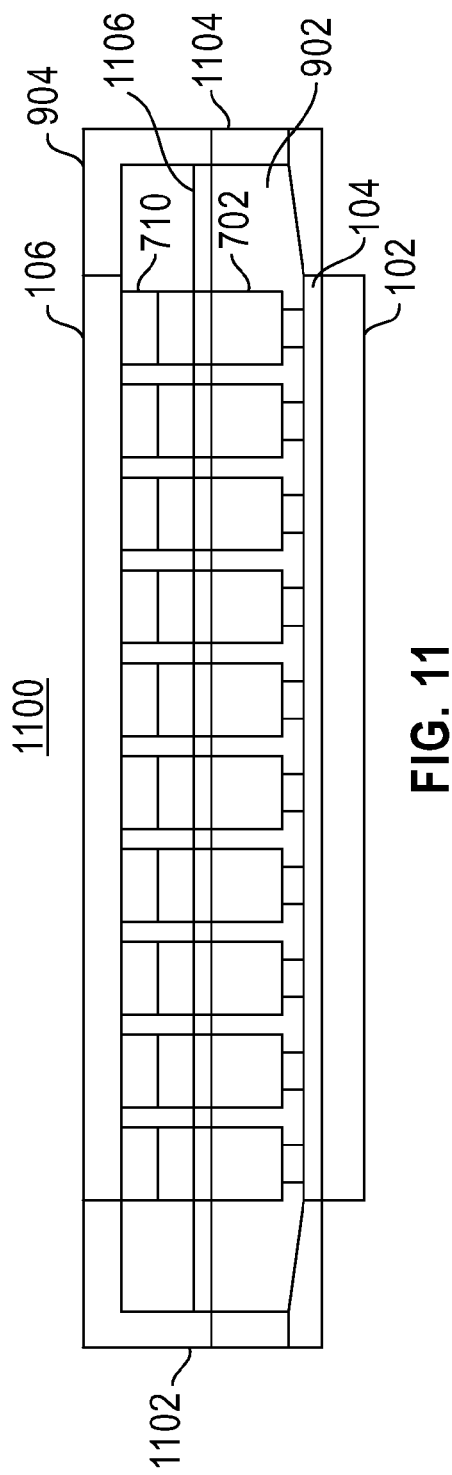
FIG. 11 is a cross-sectional side view of a cooling structure for an electronic device, the cooling structure including spring elements with a fin, a plate, a seal and a liquid, according to one embodiment of the present invention.

FIG. 11 is a cross-sectional side view of a cooling structure for an electronic device, the cooling structure including spring elements with a fin, a plate, a seal and a liquid, according to one embodiment of the present invention. FIG. 11 shows the cooling structure assembly 1100 comprising the top layer 106, the first layer 104 and the array of spring elements 710 disposed between them. FIG. 11 also shows the microprocessor 102 at the bottom of the cooling structure assembly 1100, a coolant 902, a seal 904, an internal seal 1106 and a liquid inlet/outlet pair 1102 and 1104. The cooling structure assembly 1100 of FIG. 11 is similar to the cooling structure assembly 900 of FIG. 9 except for the presence of the internal seal 1106 and the liquid inlet/outlet pair 1102 and 1104. The cooling structure 1100 can also include a pair of flow-restricting end-plates (not shown in this figure but described in greater detail below).

The internal seal 1106 provides a seal within the space filling the areas created by the gap created between the microprocessor 102 and the top layer 106. The internal seal 1106 is located at a point in the cooling structure assembly 1100 where the fin structures 702 of the array of spring elements 710 end. That is, the height of the internal seal 1106 is the height at which the fin structure 702 ends and the spring portion begins, for each of the array of spring elements 710. This is the ideal location for the internal seal 1106, as it forces the coolant 902 to travel within the area of the fin structures 702 of the array of spring elements 710, which is where a higher degree of heat dissipation occurs in the cooling structure assembly 1100.

FIG. 11 also shows an inlet/outlet pair 1102 and 1104. The inlet 1102 allows for the intake of the coolant 902 as it is pumped or otherwise pushed or propelled into the assembly 1100. As the coolant 902 travels in the space filling the areas created by the gap created between the microprocessor 102 and the top layer 106 (namely, the area of the fin structures 702 of the array of spring elements 710), the coolant 902 absorbs the heat emanated from the first layer 104 and the fin structures 702 of the array of spring elements 710. The outlet 1104 allows for the egress of the coolant 902 as it is pumped or otherwise pulled or propelled out of the assembly 1100 for cooling and eventual recycling into the assembly 1100.

Figure 12:
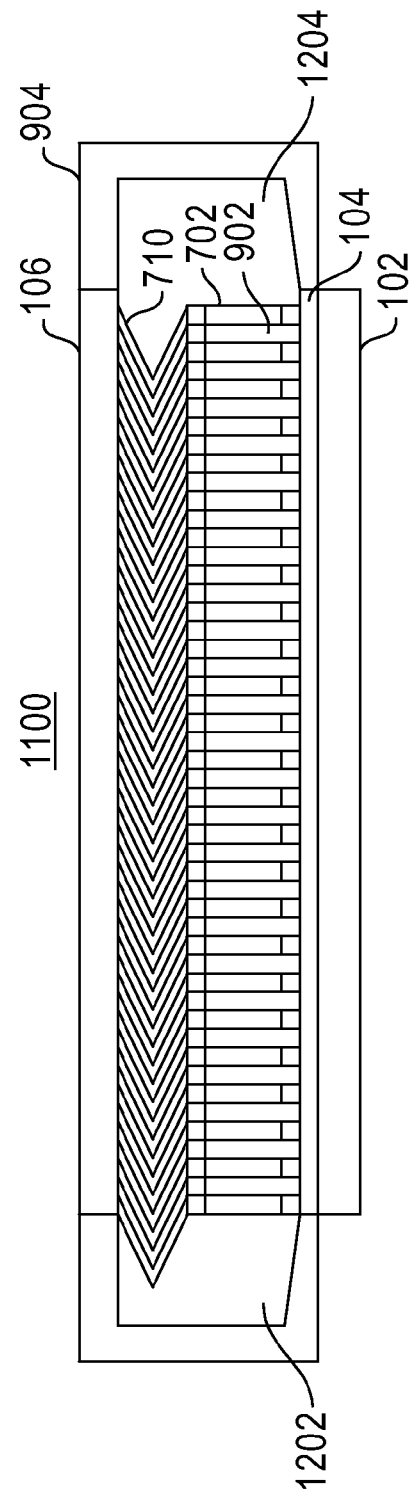
FIG. 12 is another cross-sectional side view of the cooling structure of FIG. 11.

FIG. 12 is another cross-sectional side view of the cooling structure of FIG. 11. FIG. 12 shows the cooling structure assembly 1100 comprising the top layer 106, the first layer 104 and the array of spring elements 710 disposed between them. FIG. 12 also shows the microprocessor 102 at the bottom of the cooling structure assembly 1100, a thermal interface material 902, a seal 904 and an internal seal 1106. The cooling structure 1100 can also include a pair of flow-restricting end-plates 1202 and 1204 that fill the area on either end of the array of spring elements 710 in FIG. 12. The purpose of the end-plates 1202 and 1204 is to restrict the flow of the coolant 902 into those spaces so as to force the coolant 902 to flow in the area between the multiple spring elements, which is where a higher degree of heat dissipation occurs.

FIG. 13 is a cross-sectional side view of a cooling structure for an electronic device, the cooling structure including spring elements with a fin, a plate, inlets/outlets and a coolant, according to one embodiment of the present invention. FIG. 13 shows the cooling structure assembly 1300 comprising the top layer 106, the first layer 104 and the array of spring elements 710 disposed between them. FIG. 13 also shows the microprocessor 102 at the bottom of the cooling structure assembly 1100, a coolant 902, a seal 904 and a series of inlets/outlets. The cooling structure assembly 1300 of FIG. 13 is similar to the cooling structure assembly 1100 of FIG. 1 except for the presence of the series of inlets/outlets and the lack of the internal seal 1106. The cooling structure 1300 can also include a pair of flow-restricting end-plates (not shown in this figure but described in greater detail below).

FIG. 13 also shows a series of inlets/outlets. Orifices 1302, 1304, 1306, 1308, 1310 and 1312 are designated as inlets. Orifices 1314, 1316, 1318, 1320 and 1322 are designated as outlets. The inlets allow for the intake of the coolant 902 as it is pumped or otherwise pushed or propelled into the assembly 1300. As the coolant 902 travels in the space filling the areas created by the gap created between the microprocessor 102 and the top layer 106 (namely, the area of the array of spring elements 710), the coolant 902 absorbs the heat emanated from the first layer 104 and the array of spring elements 710. The outlets allow for the egress of the coolant 902 as it is pumped or otherwise pulled or propelled out of the assembly 1300 for cooling and eventual recycling into the assembly 1300.

FIG. 14 is another cross-sectional side view of the cooling structure of FIG. 13. FIG. 14 shows the cooling structure assembly 1300 comprising the top layer 106, the first layer 104 and the array of spring elements 710 disposed between them. FIG. 14 also shows the microprocessor 102 at the bottom of the cooling structure assembly 1300, a coolant 902 and a seal 904. The cooling structure 1300 can also include a pair of flow-restricting end-plates 1402 and 1404 that fill the area on either end of the array of spring elements 710 in FIG. 14.

Figure 15:
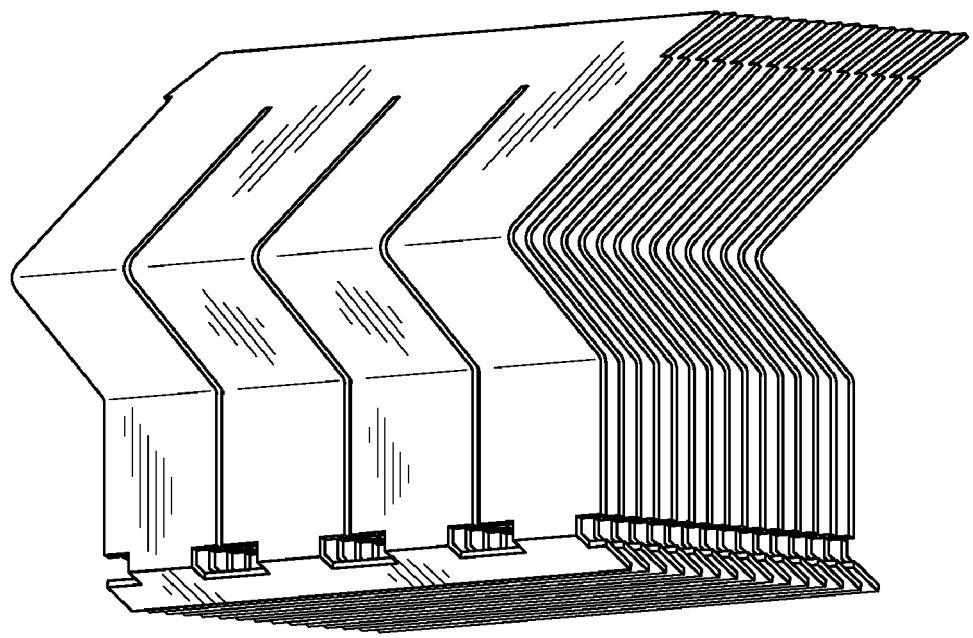
FIG. 15 is a perspective view of a series of spring elements in a stacked arrangement.

FIG. 15 is a perspective view of a series of spring elements in a stacked arrangement. A uniform first distance exists between each spring element. Note each of the spring elements comprises a single sheet of material, such as a thermally conductive sheet of metal such as copper, that includes sections that are drilled out or removed. The spring elements of FIG. 15 are examples of spring elements that can be used in any of the cooling structure assemblies 100, 300, 500, 700, 900, 1100 and 1300. The stacked nature of the spring elements of FIG. 15 show how the spring elements can be arranged for inclusion into any of the aforementioned cooling structure assemblies. Note that FIGS. 15-17 show the series of spring elements as they are stacked during assembly of a microprocessor assembly that includes the present invention, in one embodiment.

Figure 16:
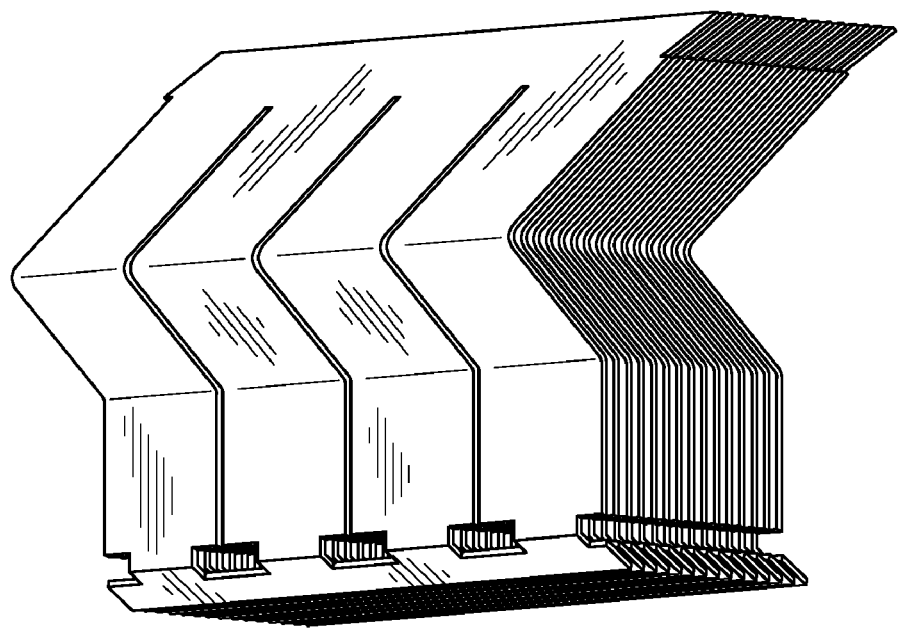
FIG. 16 shows the spring elements of FIG. 15 in a tighter stacked arrangement.
Figure 17:
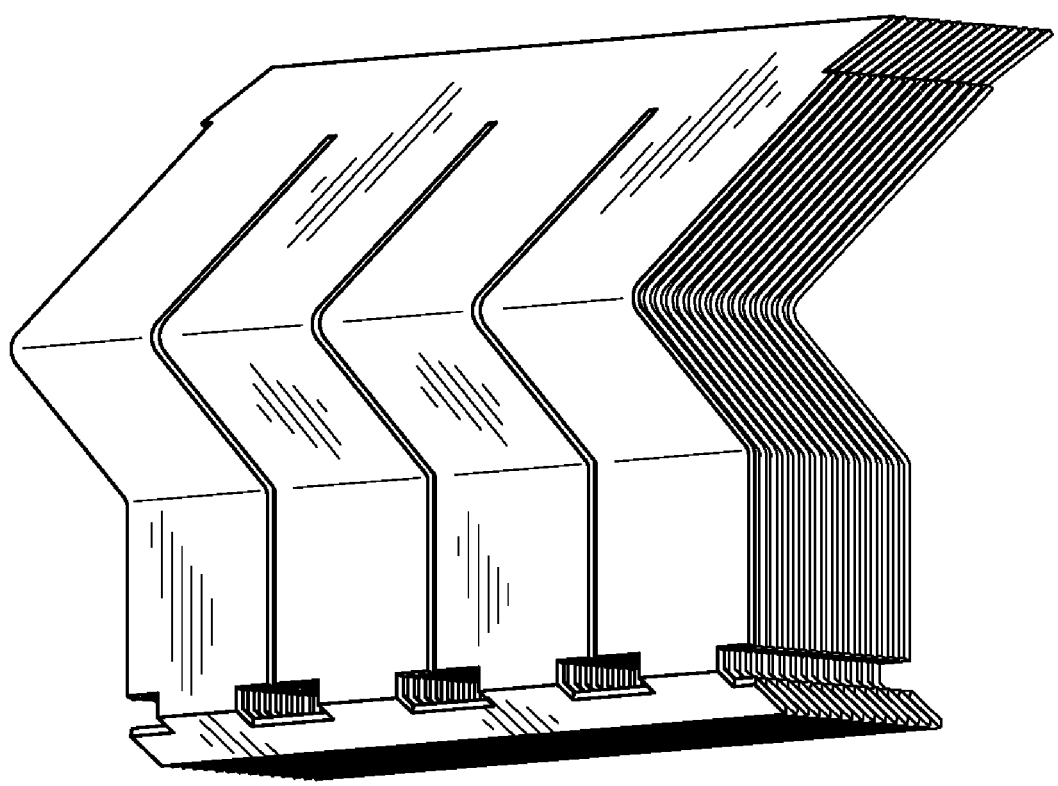
FIG. 17 shows the spring elements of FIG. 15 in an even tighter stacked arrangement.

FIG. 16 shows the spring elements of FIG. 15 in a tighter stacked arrangement. A uniform second distance exists between each spring element, wherein the second distance is shorter than the first distance. FIG. 17 shows the spring elements of FIG. 15 in an even tighter stacked arrangement. A uniform third distance exists between each spring element, wherein the third distance is shorter than the second distance.

Figure 18:
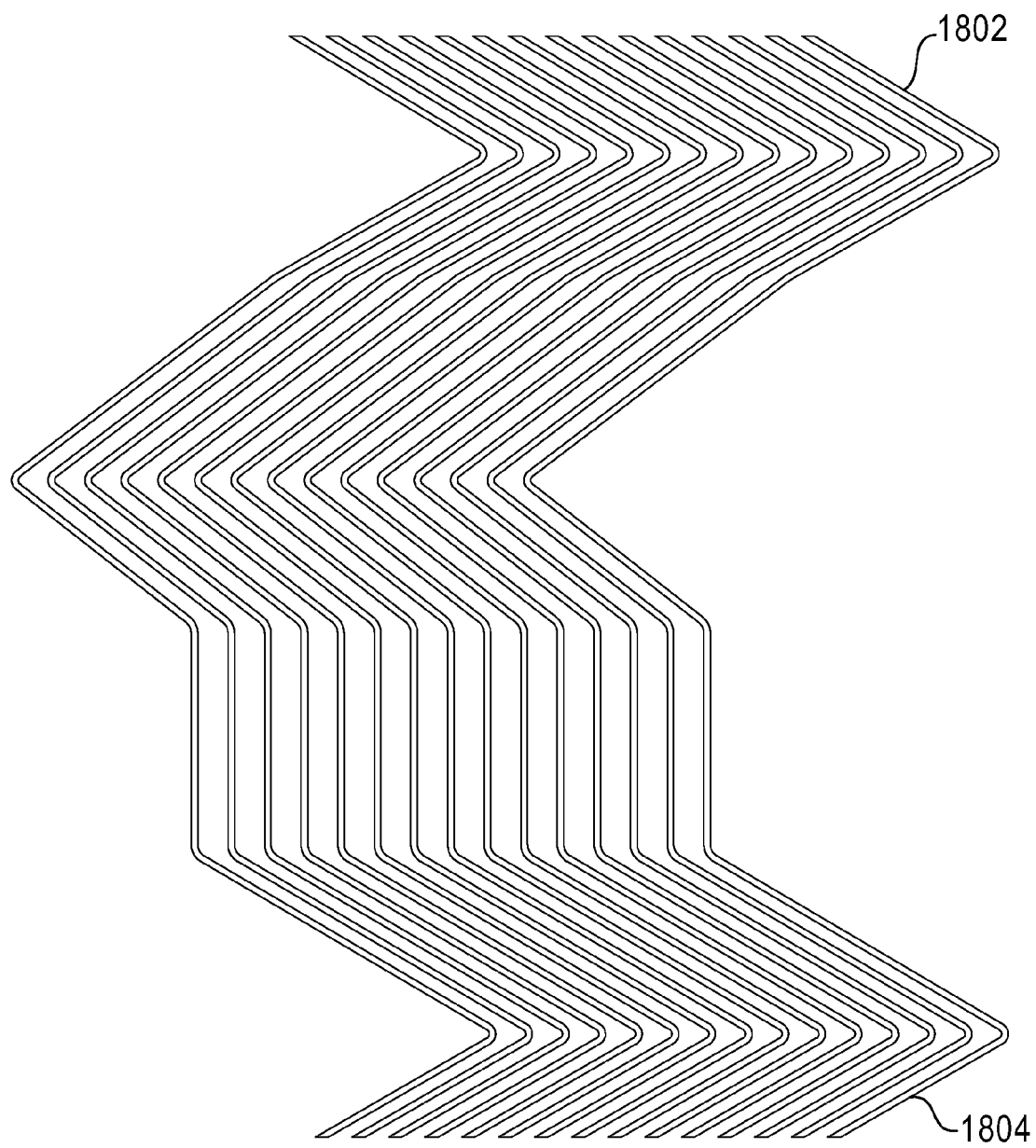
FIG. 18 is a cross-sectional side view of spring elements in a stacked arrangement.

FIG. 18 is a cross-sectional side view of spring elements in a stacked arrangement. A uniform first distance exists between each spring element. Compared to the spring elements of FIG. 15, note that the spring elements of FIG. 18 each include an additional element 1802 on the top end of the spring elements and an additional element 1804 on the bottom end of the spring elements. Note that FIGS. 18-20 show the series of spring elements as they are stacked during assembly of a microprocessor assembly that includes the present invention, in one embodiment.

Figure 19:
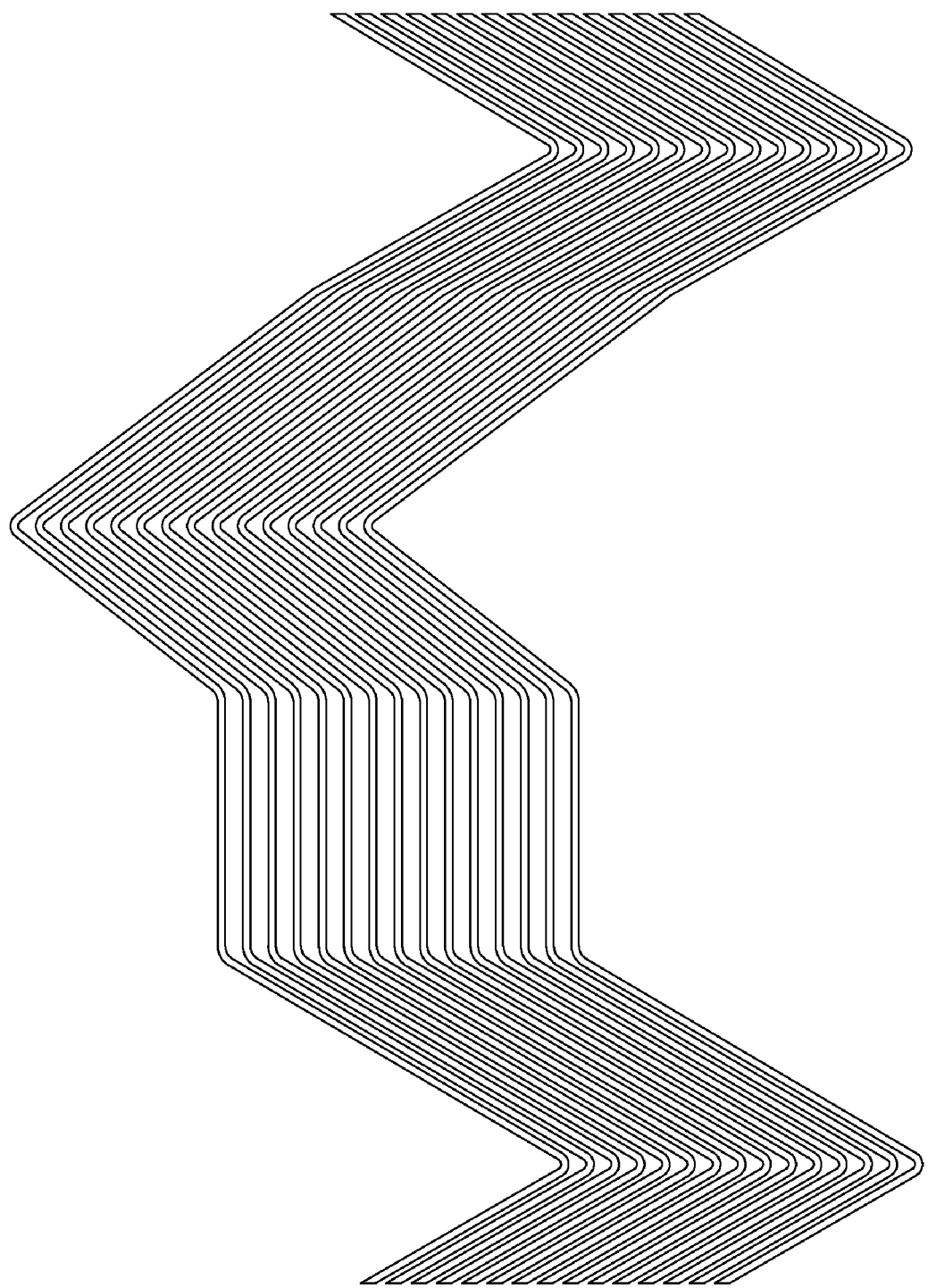
FIG. 19 shows the spring elements of FIG. 18 in a tighter stacked arrangement.
Figure 20:
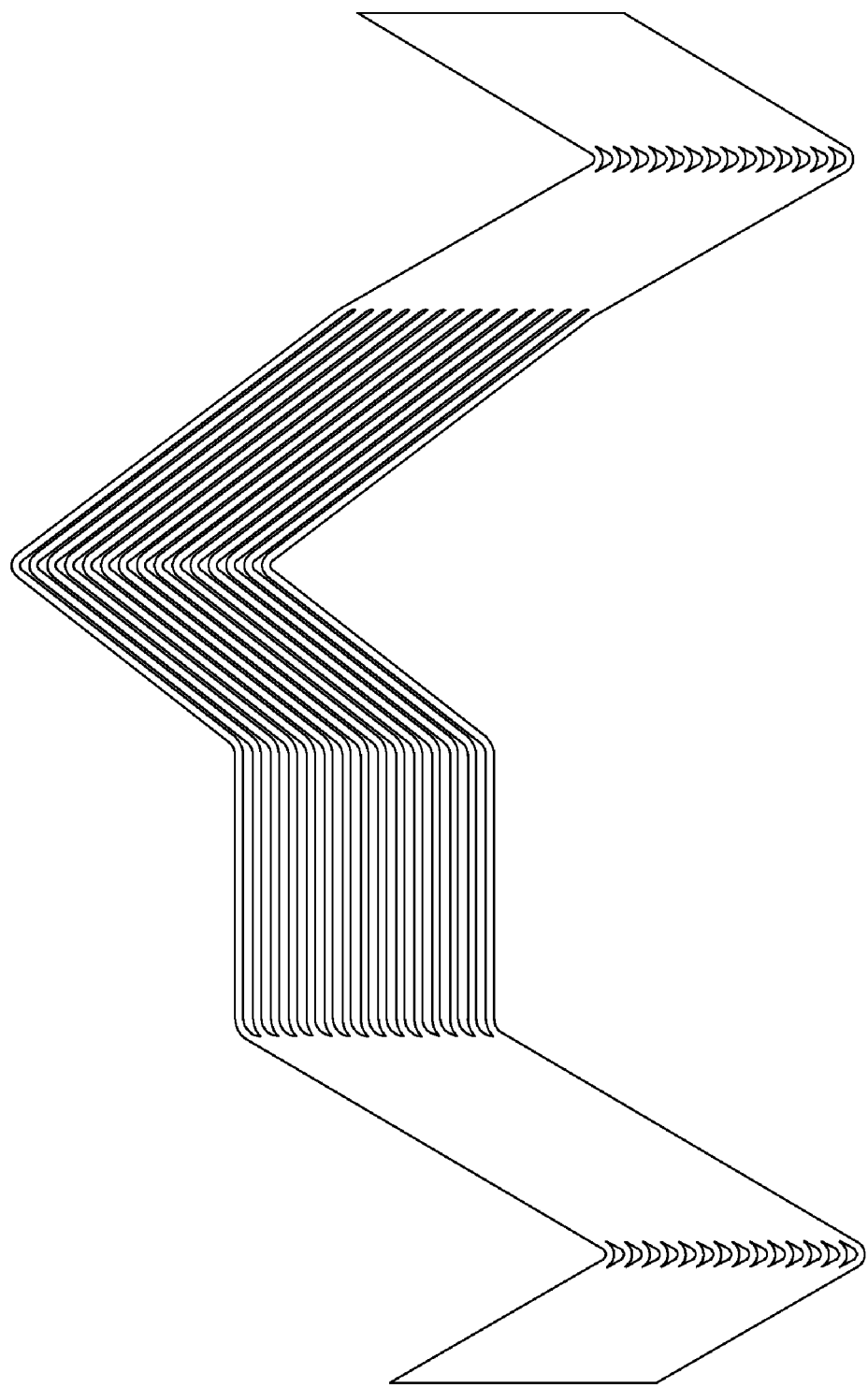
FIG. 20 shows the spring elements of FIG. 18 in an even tighter stacked arrangement.
Figure 21:
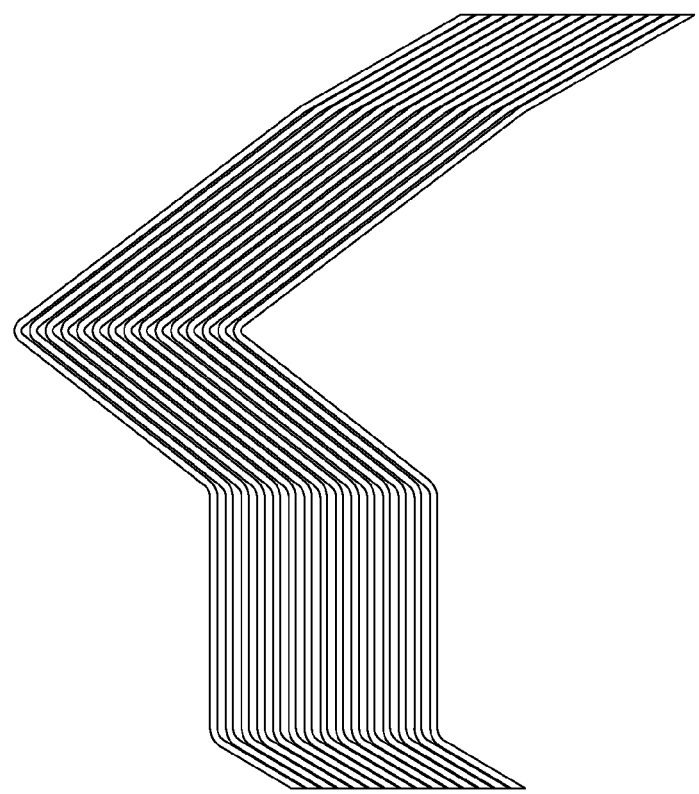
FIG. 21 shows the spring elements of FIG. 18 in an even tighter stacked arrangement.

FIG. 19 shows the spring elements of FIG. 18 in a tighter stacked arrangement. A uniform second distance exists between each spring element, wherein the second distance is shorter than the first distance. FIG. 20 shows the spring elements of FIG. 18 in an even tighter stacked arrangement. A uniform third distance exists between each spring element, wherein the third distance is shorter than the second distance. FIG. 21 shows the spring elements of FIG. 18 in an even tighter stacked arrangement. A uniform fourth distance exists between each spring element, wherein the fourth distance is shorter than the third distance. Note in FIG. 21 that the additional element 1802 on the top end of the spring elements and the additional element 1804 on the bottom end of the spring elements has been removed. That is, the spring elements have been trimmed.

Figure 22:
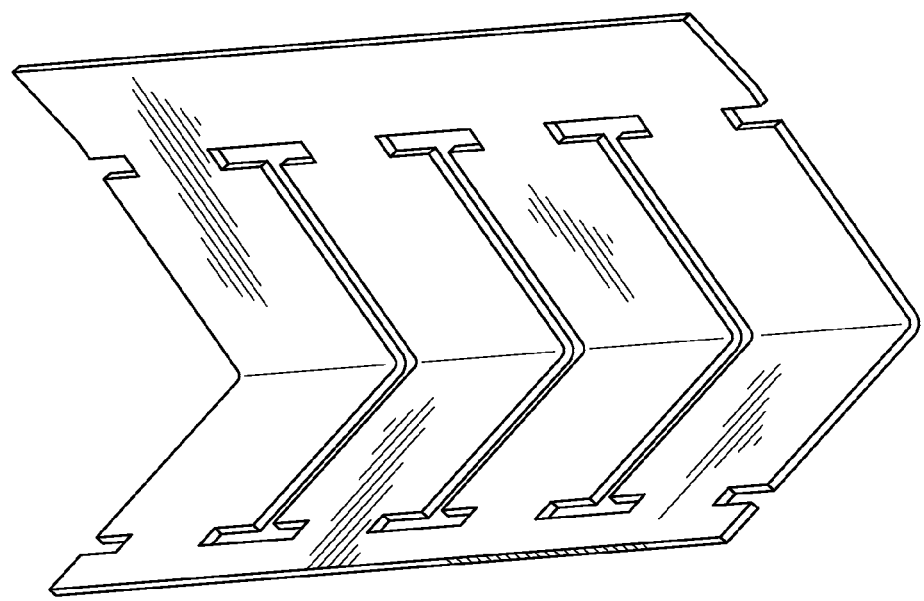
FIG. 22 is a perspective view of a spring element.
Figure 23:
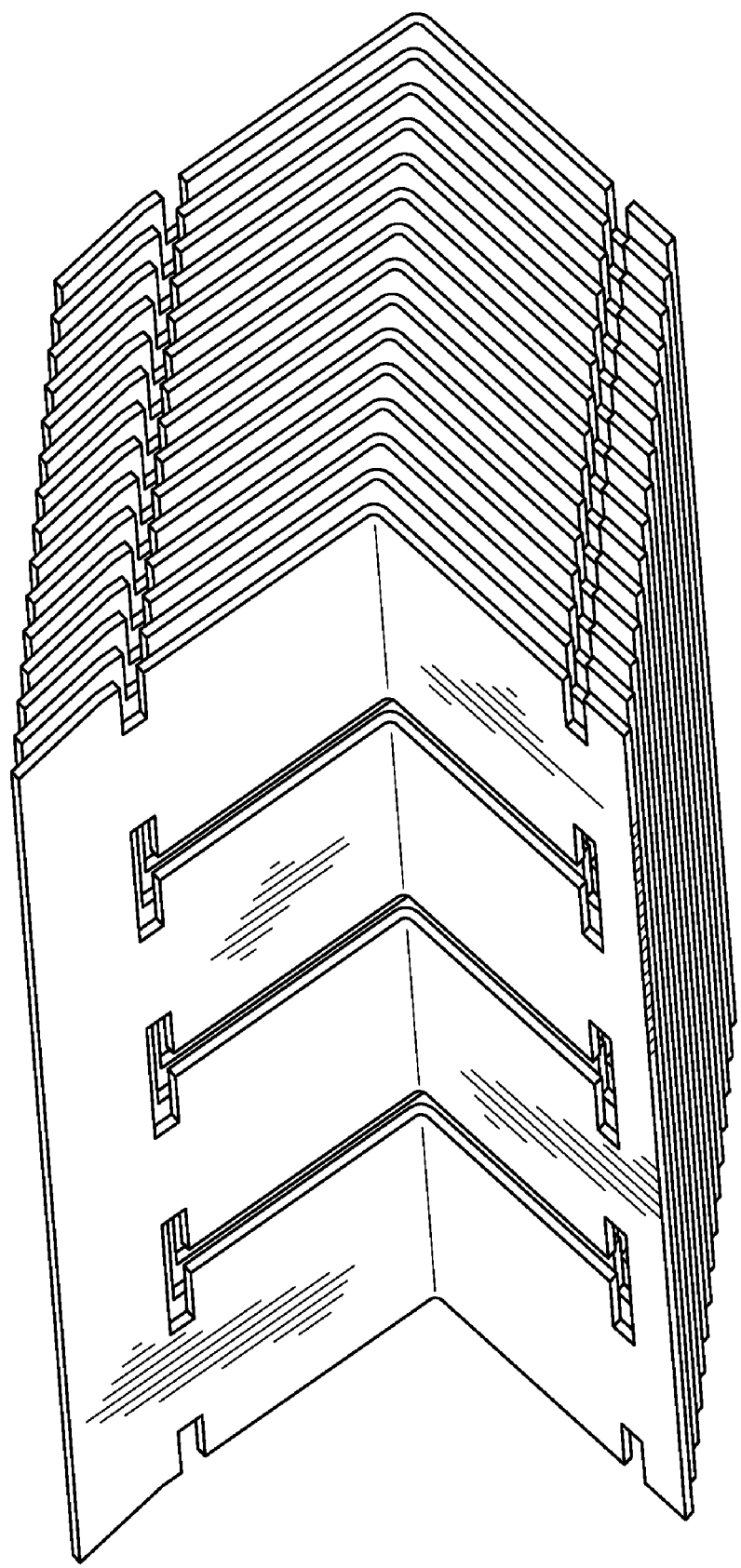
FIG. 23 is a perspective view of a series of spring elements of FIG. 22 in a stacked arrangement.

FIG. 22 is a perspective view of a spring element. Note that the spring element comprises a single sheet of material, such as a thermally conductive sheet of metal such as copper, that includes sections that are drilled out or removed. The spring element of FIG. 15 is an example of a spring element that can be used in any of the cooling structure assemblies 100, 300, 500, 700, 900, 1100 and 1300. FIG. 23 is a perspective view of a series of spring elements of FIG. 22 in a stacked arrangement. A uniform first distance exists between each spring element. The stacked nature of the spring elements of FIG. 23 show how the spring elements can be arranged for inclusion into any of the aforementioned cooling structure assemblies.

Figure 24:
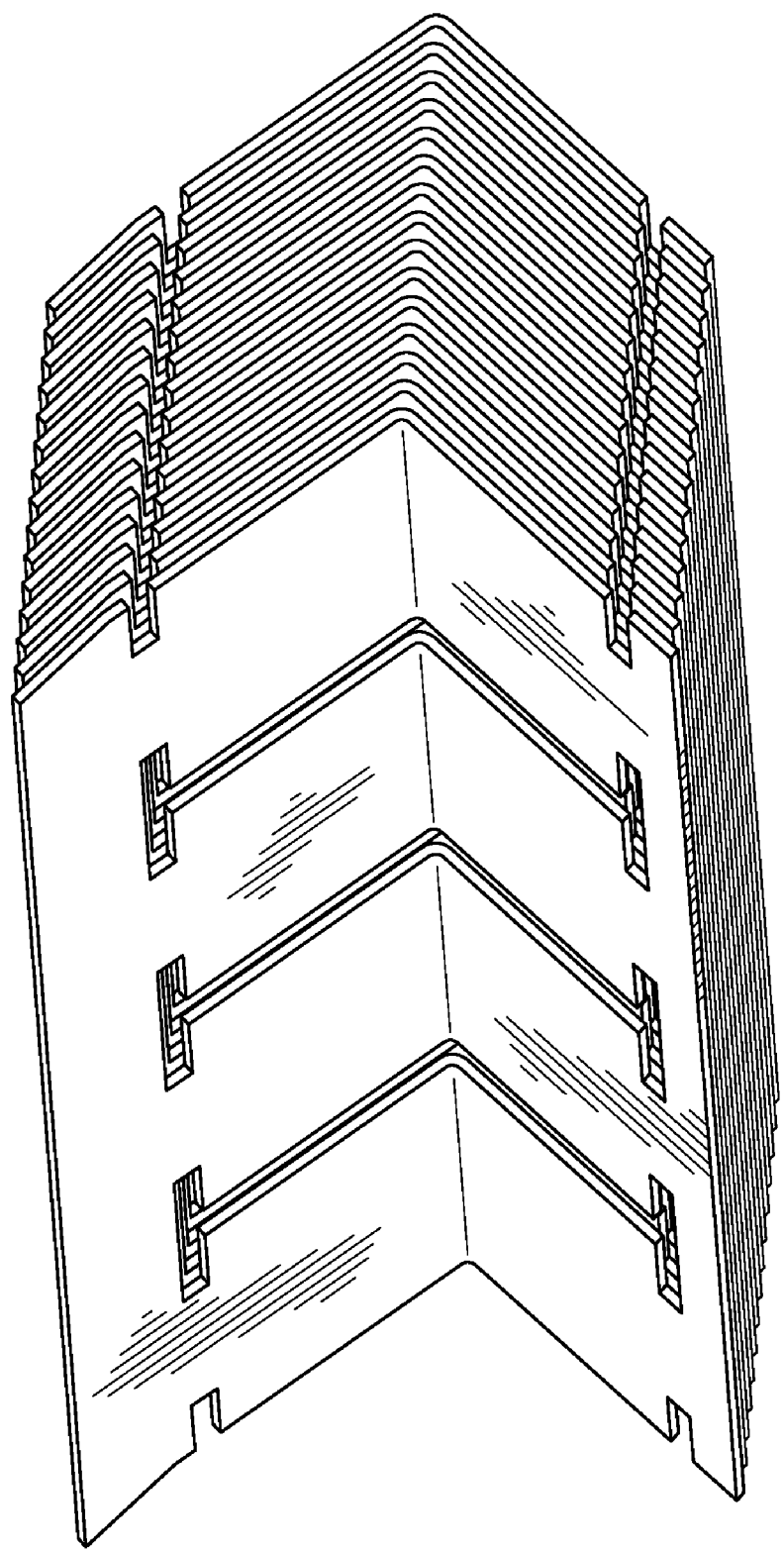
FIG. 24 shows the spring elements of FIG. 23 in a tighter stacked arrangement.
Figure 25:
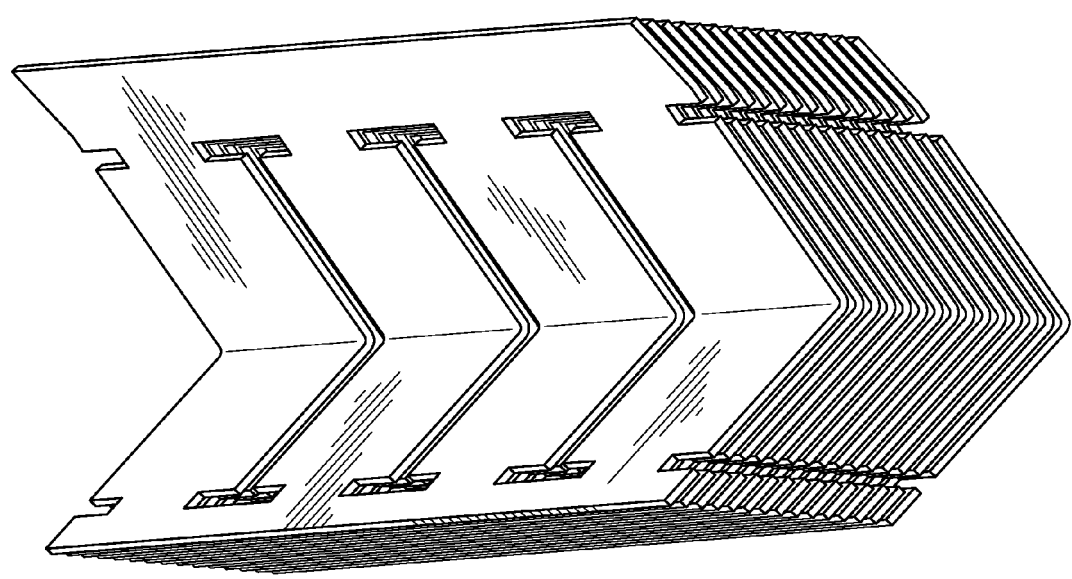
FIG. 25 shows the spring elements of FIG. 23 in an even tighter stacked arrangement.

FIG. 24 shows the spring elements of FIG. 23 in a tighter stacked arrangement. A uniform second distance exists between each spring element, wherein the second distance is shorter than the first distance. FIG. 25 shows the spring elements of FIG. 23 in an even tighter stacked arrangement. A uniform third distance exists between each spring element, wherein the third distance is shorter than the second distance.

Figure 26:
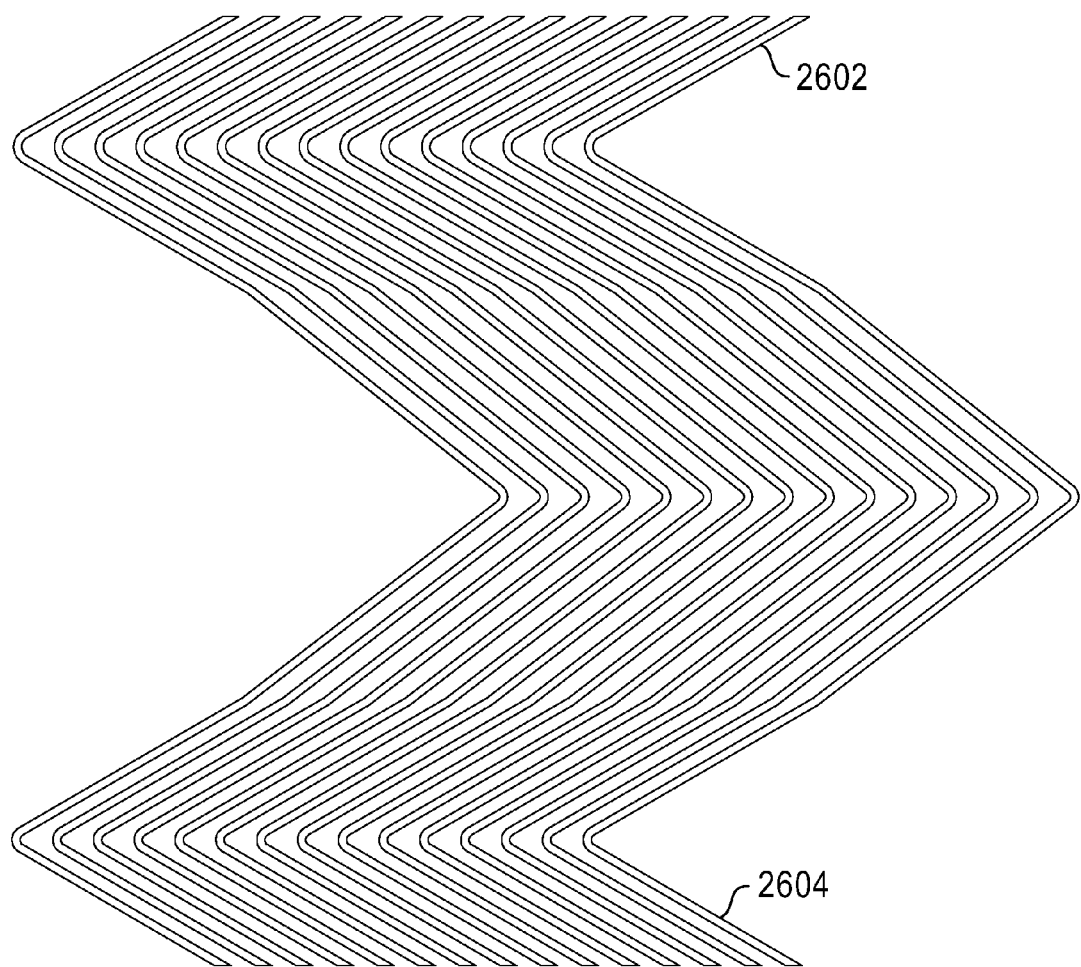
FIG. 26 is a cross-sectional side view of spring elements in a stacked arrangement.
Figure 27:
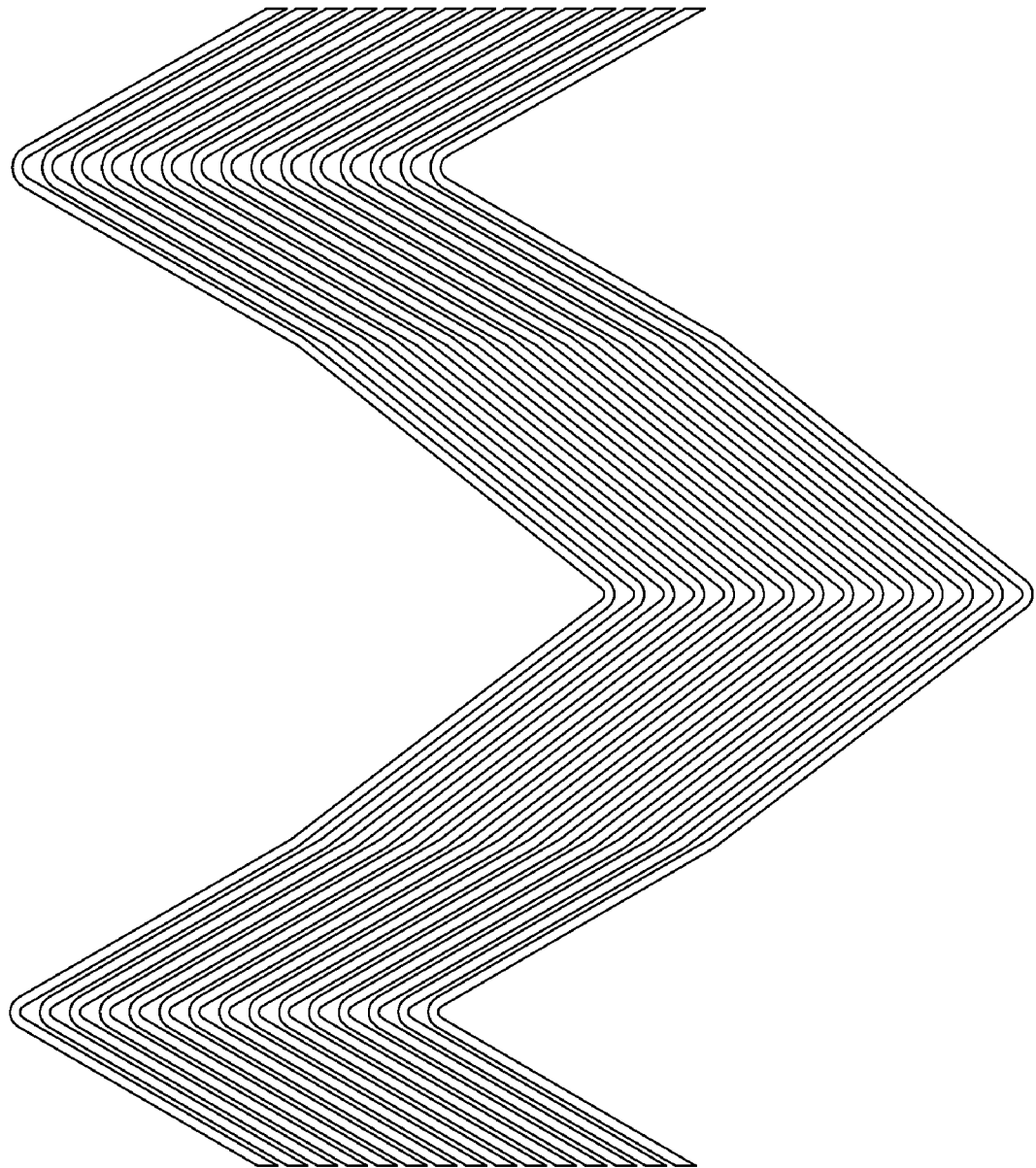
FIG. 27 shows the spring elements of FIG. 26 in a tighter stacked arrangement.
Figure 28:
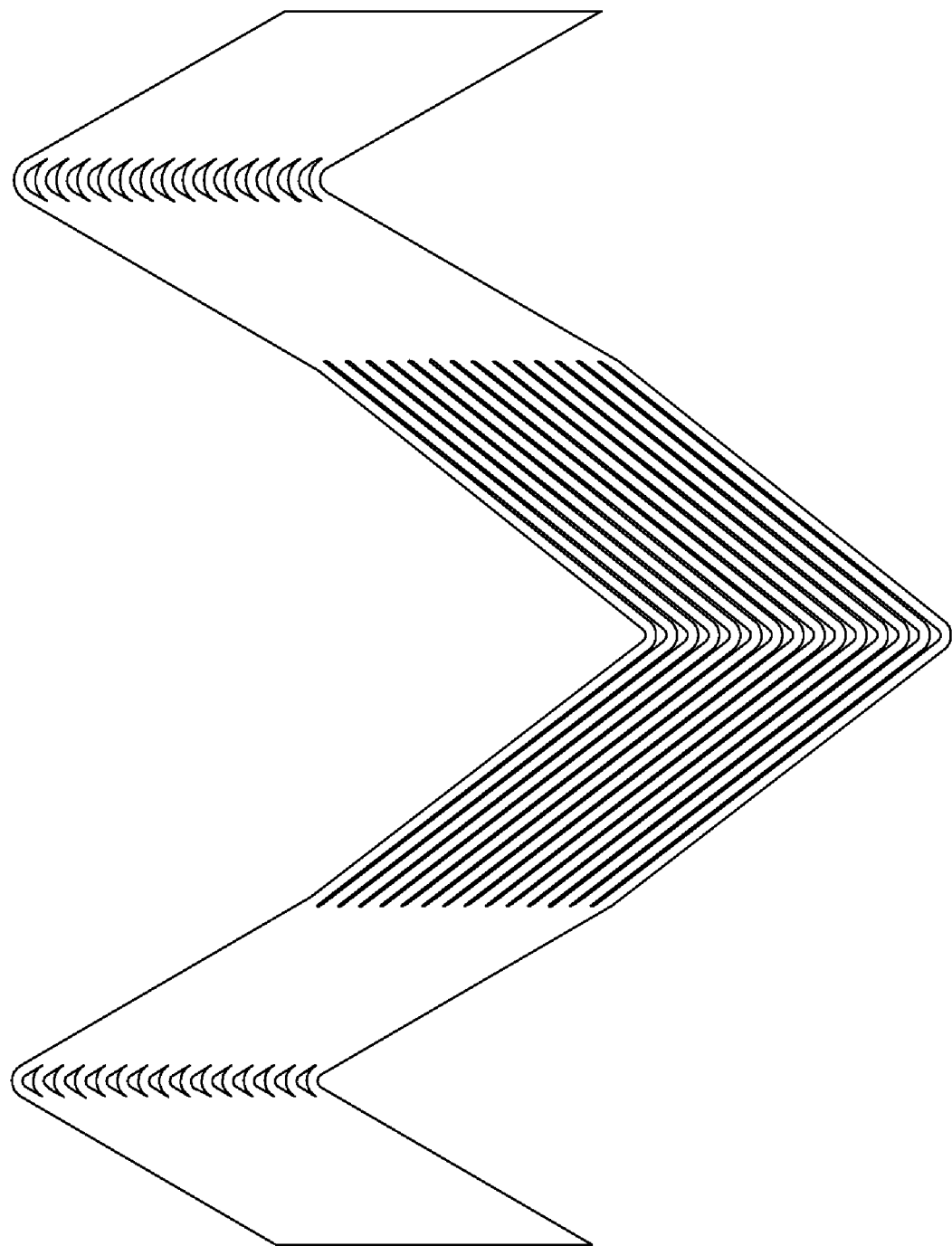
FIG. 28 shows the spring elements of FIG. 26 in an even tighter stacked arrangement.
Figure 29:
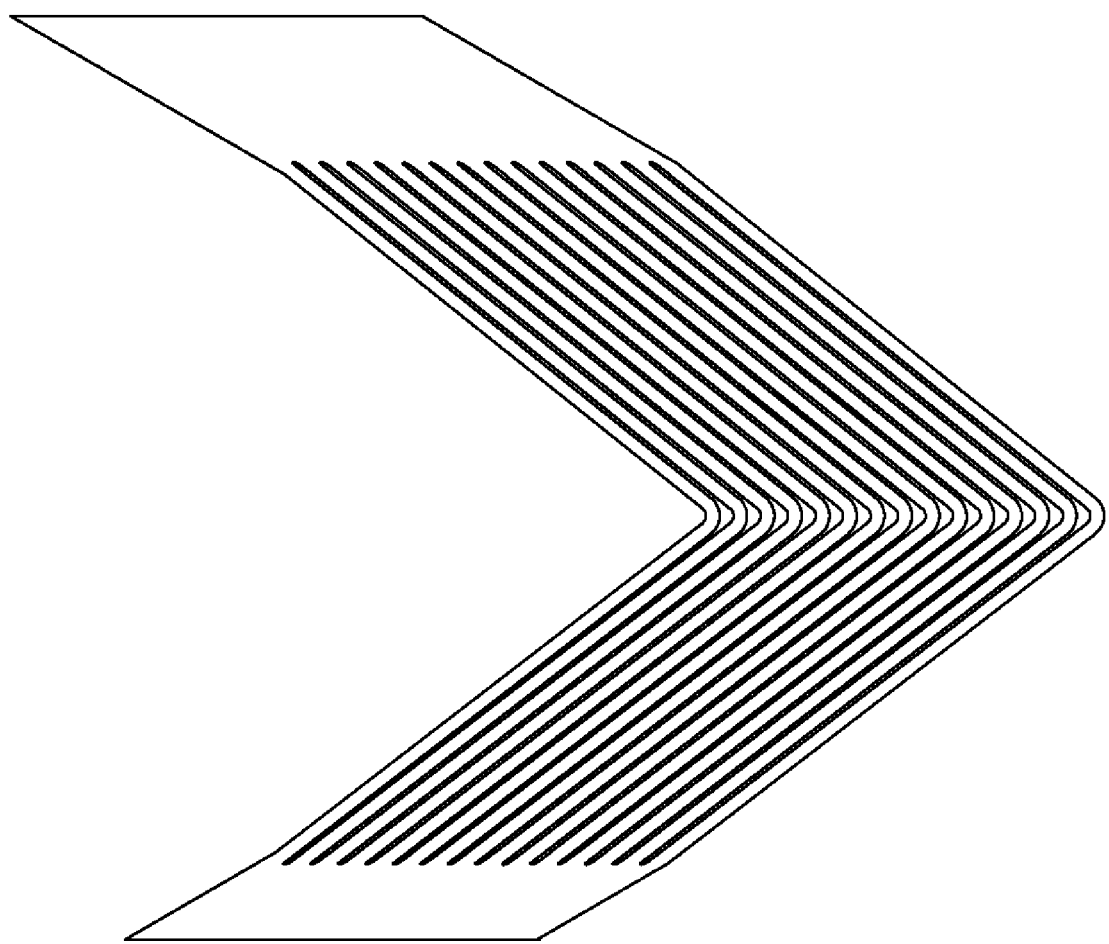
FIG. 29 shows the spring elements of FIG. 26 in an even tighter stacked arrangement.

FIG. 26 is a cross-sectional side view of spring elements in a stacked arrangement. A uniform first distance exists between each spring element. Compared to the spring elements of FIG. 23, note that the spring elements of FIG. 26 each include an additional element 2602 on the top end of the spring elements and an additional element 2604 on the bottom end of the spring elements. FIG. 27 shows the spring elements of FIG. 26 in a tighter stacked arrangement. A uniform second distance exists between each spring element, wherein the second distance is shorter than the first distance. FIG. 28 shows the spring elements of FIG. 26 in an even tighter stacked arrangement. A uniform third distance exists between each spring element, wherein the third distance is shorter than the second distance. FIG. 29 shows the spring elements of FIG. 26 in an even tighter stacked arrangement. A uniform fourth distance exists between each spring element, wherein the fourth distance is shorter than the third distance. Note in FIG. 29 that the additional element 2602 on the top end of the spring elements and the additional element 2604 on the bottom end of the spring elements has been removed.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

We claim:

1. A structure for cooling an electronic device, the structure comprising:
   a solid heat-conducting layer comprising a planar surface;
   a plurality of copper spring elements with a high packing density, said plurality of copper spring elements integrated with the solid heat-conducting layer for providing a heat path from the electronic device, and
   a very thin thermal interface material disposed between the plurality of copper spring elements and the electronic device;
   wherein the plurality of copper spring elements extend in an upper direction away from the electronic device and wherein the plurality of copper spring elements comprise a spring for offering resistance when loaded such that the copper spring elements exhibit qualities of a spring, allowing for compression and elongation in the x, y, and z directions and
   wherein at least one of the plurality of copper spring elements has a smaller contact area at a first end, wherein said contact area gradually increases in cross section to a full cross section of the copper spring element at a second end in contact with the thermal interface material, to prevent the first end of the spring element from adding unwanted rigidity to the structure for cooling with minimal thermal resistance.

2. The structure of claim 1 wherein the solid heat-conducting layer comprises one of a thermally conductive adhesive and a solder.

3. The structure of claim 2 wherein the solder comprises indium.

4. The structure of claim 1 wherein the solid heat-conducting layer comprises a copper sheet.

5. The structure of claim 1 wherein the first end of each of the plurality of spring elements is narrowed.

* * * * *